United States Patent [19]

Burstein

[11] 3,977,398

[45] Aug. 31, 1976

[54] FLUTED SUB-TROCHANTERIC NAIL SYSTEM

[75] Inventor: Albert H. Burstein, Shaker Heights, Ohio

[73] Assignee: The Sampson Corporation, Pittsburgh, Pa.

[22] Filed: Jan. 12, 1976

[21] Appl. No.: 648,091

[52] U.S. Cl. ............................................. 128/92 BC
[51] Int. Cl.² ...................... A61F 5/04; A61B 17/18
[58] Field of Search ............ 128/92 R, 92 B, 92 BA, 128/92 BB, 92 D, 92 EC

[56] References Cited
UNITED STATES PATENTS

| | | | |
|---|---|---|---|
| 2,537,070 | 1/1951 | Longfellow | 128/92 BA |
| 3,783,860 | 1/1974 | Burstein et al. | 128/92 BC |
| 3,892,233 | 7/1975 | Vestby | 128/92 BA |

FOREIGN PATENTS OR APPLICATIONS

| | | | |
|---|---|---|---|
| 1,031,128 | 3/1953 | France | 128/92 BC |

OTHER PUBLICATIONS

"Fluted Intramedullary Rod System" by Sampson, pamphlet by The Sampson Corp., Printed July, 1974 in U.S.A.

Primary Examiner—Ronald L. Frinks
Attorney, Agent, or Firm—Dennison, Dennison, Meserole & Pollack

[57] ABSTRACT

A sub-trochanteric intramedullary rod for use in fracture fixation in the femur characterized in that it is fluted throughout its length and has a minor portion of a diameter greater than its major portion, thereby being of stepped configuration. The distal ends of the flutes in each of the major and minor portions have sharp points thereon adapted to cut into bone and means are provided beneath the points to receive bone particles and chips cut by the points.

12 Claims, 7 Drawing Figures

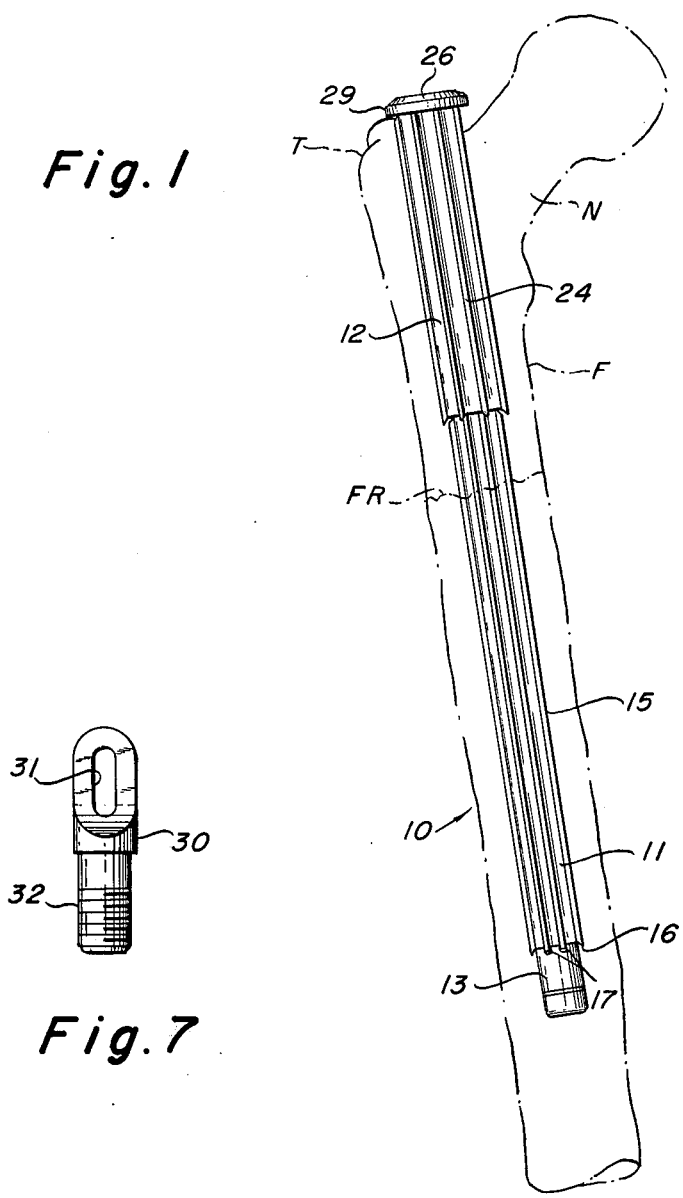
Fig. 1
Fig. 7
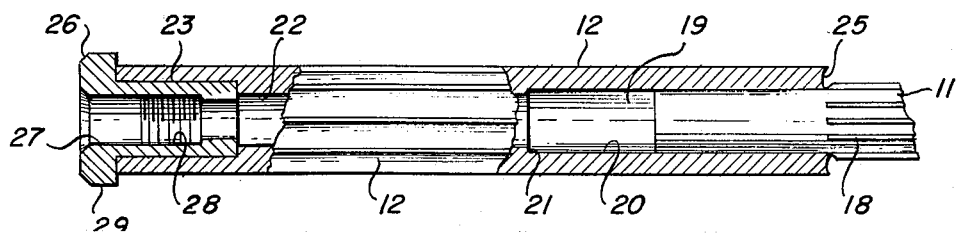
Fig. 6

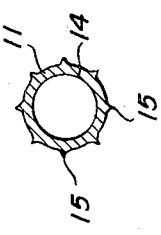
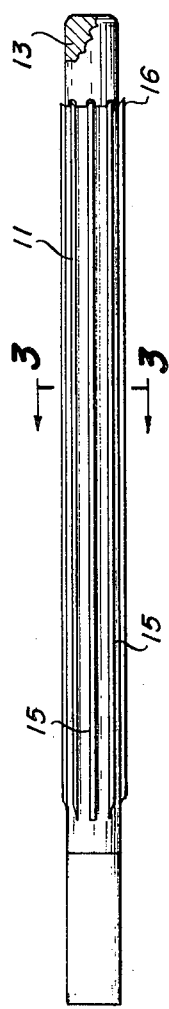
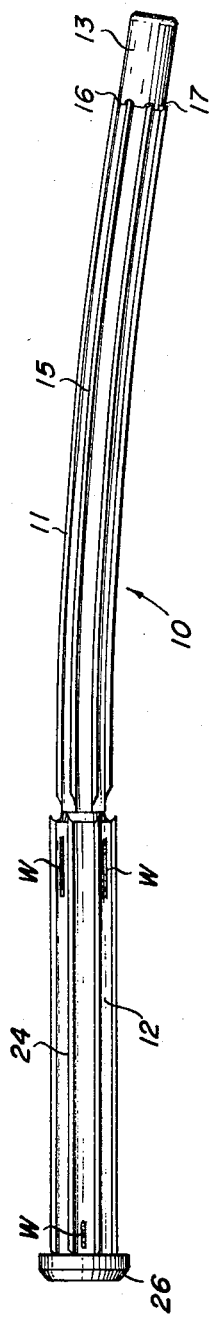

FLUTED SUB-TROCHANTERIC NAIL SYSTEM

BACKGROUND OF THE INVENTION

This invention relates generally to a new device for use in orthopaedic surgery and more specifically to a new sub-trochanteric intramedullary rod system for use in fixation of fractures surgically for the purpose of maintaining the fractured portions of long bones together, and principally useful in fractures of the femur involving the sub-trochanteric and proximal shaft areas.

In the field of orthopaedic surgery, it has become common practice in many situations to use as a fracture fixation means an elongated rod or nail commonly known in the art as an intramedullary rod. Such a rod is driven into the marrow cavity or medullary passage longitudinal in a fractured bone after lateral reduction and serves to hold the severed parts thereof in longitudinal alignment incident to knitting and healing of the bone. Such nails or rods are used in treatment of long bone fractures, for example in the treatment for fracture of the femur. The nail or rod in such cases is driven percutaneously longitudinally through the tip or trochanter and into the medullary canal, and therefore serves to bridge the area of fracture in the stem on either side thereof.

Intramedullary rods are known in various forms but it has proven most satisfactory in obtaining a solid and secure joinder of fractured bones to use a rod or nail which is not subject to twisting or turning within the medullary passage of the bone. The ideal function of an intramedullary rod is to secure the proximal and distal fragments of the bone which has been fractured in correct alignment during the healing process. It should be noted that several types of loads must be transmitted from the distal to the proximal fragments. These include: compression, bending, and torsion. The compression loads are transmitted generally directly through the bone surface, while torsional and bending loads are transmitted, at least in part, by the intramedullary rod itself. In order to properly transmit torque, the rod or nail must be capable of securely gripping both the proximal and distal fragments. Additionally, the nail must be sufficiently rigid to prevent excessive bending motion at the fracture site.

The invention disclosed herein is a modification of that shown in the Burstein et al U.S. Pat. No. Re. 28,502 and has been specifically designed for fixation of sub-trochanteric femoral fractures, that is, those fractures distal to the trochanter and the femur, but proximal to the junction of the middle third and proximal third. It is recognized that sub-trochanteric femoral fractures generally occur in an area of the femur which, under normal load applications, is subjected to extremely high bending loads. The bending loads and the extremely large torsional loads present when the femur is fractured today present one of the most difficult surgical management problems in fracture fixation. Any internal fixation device to be employed for stabilizing these fractures until healing occurs, must be sufficiently strong to resist these bending loads while maintaining proper axial alignment of the bone segments.

DESCRIPTION OF THE PRIOR ART

In general three types of internal fixation devices are in use today.

NAIL-IMPLANT COMBINATION DEVICES

While historically many of these common hip nail devices have been used, there has recently been a move to the use of stronger or built up versions of this type device. Attention is directed to the well known Holt nail. In all of the known devices of this type, the method of insertion and the short-comings are similar. The nail portion of the device is generally inserted into the neck of the femur with the plate portion attached to the femoral shaft with bone screws. Thus, the proximal fragment is held by the nail portion and the distal fragment held by the plate portion. In this regard, attention is directed to the patent to Collison U.S. Pat. No. 2,612,159 and the patent to Price U.S. Pat. No. 2,627,855, which are typical examples of devices of this type.

In many cases, the plate portion will of necessity be quite long in order to enable a sufficient number of bone screws to be attached to the distal fragment. Depending upon the type and location of the fracture, and particularly the type of device to be used, it may not always be possible to place any screws in the proximal fragment even though the plate is in contact with the femoral shaft.

Among other shortcomings of devices of this type are (1) that it is limited to an open surgical procedure and requires a large operative exposure; (2) the final rotational stability depends on the major involvement of a nonfractured element, namely the neck of the femur; (3) there are inherent weaknesses of devices of this type in the nail-plate junction; and (4) plate bending or failure is quite common and inevitably occurs either at or near a screw hole in the area of maximum stress, and hence union of the sub-trochanteric fracture is typically slow. Additionally, the typical flat plate section is not well adapted for resisting the torsional forces usually present in sub-trochanteric fractures treated with this type of device. Later removal of the device of course requires another open procedure and a similar operative exposure, and the removal of the bone screws frequently will seriously weaken the bone at each of the screw holes.

NAIL-NAIL COMBINATION DEVICES

The patent to Zickel U.S. Pat. No. 3,433,220 is typical of another form of intramedullary rod used for treatment of femoral fractures and consists of a two piece device which is wholly intramedullary. The longer component is inserted into the medullary canal of the femur and the shorter component is inserted through a cross opening in the longer component and into the neck of the femur. A set screw is then inserted into the top of the longer component to lock the shorter component in place. Devices of the Zickel type are limited to an open procedure which, though requiring a somewhat smaller operative site than that disclosed above, involves the precise and laborious use of jigs or other fixtures to correctly align the two components and to lock them together. Here again, the device requires the major involvement of a nonfractured element, the neck of the femur, in order to provide rotational stability. It should also be noted that the longer component of the Zickel rod, while providing axial alignment, is not capable of providing sufficient rotational stability, and at best provides only marginal bending strength.

BONE PLATE DEVICES

The third solution to treatment of femoral fractures of the type noted involves the use of long, heavy and sometimes complex compression bone plates to span the fracture site. In order to accommodate the low density cancellous bone in the proximal fragment, cancellous or lag type bone screws are used in the proximal plate section and normal or cortical bone screws are used in the distal section. Typically, plates employed for this purpose are of necessity rather long so that a sufficient number of screws can be used both proximally and distally to the site of the fracture. If the plate is not prebent in the proximal section, the surgeon may do so and could thereby compromise the original fatigue strength of the plate. Plates are also limited to an open procedure requiring an extensive operative site and removal would require a similar procedure and exposure and of course as noted above the large number of screws can, when removed, seriously weaken the bone. Single plating may provide sufficient bending strength in one plane, but an even more extensive procedure and a large number of bone screws must be used in double or right angle plating, that is, laterally and anteriorly, in order to develop greater bending strength and torsional stability.

SUMMARY OF THE INVENTION

The new fluted sub-trochanteric nail system or rod disclosed herein is designed to provide an entirely intramedullary device for the fixation of sub-trochanteric fractures which can be inserted via a closed or "blind" procedure, or via an open procedure without the necessity of X-ray surveillance, with only a minimal surgical exposure and not requiring the use of jigs, fixtures or other special instrumentation via either procedure, which provides both sufficient stability at the fracture site and resistance to high bending and torsional loads common in such fractures so that the fracture will heal as quickly as possible, and thereafter is removed with only a minimal incision being necessary and without affecting the fracture site or any portion of the femur itself.

The new sub-trochanteric rod is of generally hollow internal construction in the preferred form and is provided with a two-diameter stepped cylinder designed to entirely fill the medullary canal of the femur both proximal and distal to the fracture site. The rod or nail has two different diameter portions, each possessing its own set of flutes. The number of diameter combinations of the nail or rod is not limited but the difference between the two diameters and each nail should be preferably at least 1.5 mm. Means are provided on at least one end portion of the rod, namely the distal portion, to collect and accommodate bone chips to permit the flutes of the rod to cut grooves in the medullary canal.

An important object of the present invention is to provide a sub-trochanteric intramedullary rod having extremely high strength in bending and torsion comparable to the strength of the normal femur to thereby permit early mobility without fear of bending the nail.

It is a further object of the invention to provide a sub-trochanteric rod having a stepped or multiple diameter construction.

Yet a further object of the invention is to provide a fluted sub-trochanteric rod having cutting surfaces on the advancing edge of the longitudinal flutes of the rod to cut through the bone to prevent splitting or wedging.

It is yet another object of the invention to provide an intramedullary rod of the subtrochanteric type that has the advantage of being able to grip all about the endosteal surface of a bone without completely filling the endosteal volume.

A further object of the invention is to provide an intramedullary rod which requires minimum force for insertion since material is being cut.

A further object of the invention is the provision of a novel hollow sub-trochanteric intramedullary rod which is of generally simple construction and which is safe and efficient in use.

The above and additional objects of the invention will become apparent from a consideration of the following disclosure.

DESCRIPTION OF THE DRAWINGS

FIG. 1 is a side elevation of the sub-trochanteric rod in place in a typical femur shown in dotted outline;

FIG. 2 is a side elevation of the distal component of the sub-trochanteric rod of the present invention;

FIG. 3 is a sectional view taken on the lines 3—3 of FIG. 2;

FIG. 4 is a side elevation of the assembled sub-trochanteric rod shown rotated 90° from the position of FIG. 1;

FIG. 5 is an end view of the cap;

FIG. 6 is an enlarged partially sectional view of the proximal component of the rod showing its method of attachment to the distal portion of the rod; and FIG. 7 is an elevation of the extractor cap.

DESCRIPTION OF THE PREFERRED EMBODIMENT

The sub-trochanteric nail of the present invention is shown generally at 10 and includes a smaller diameter distal portion 11 and a larger diameter proximal portion 12. In the preferred embodiment of the invention shown in the drawings, the distal and proximal portions are formed separately and joined into assembled relationship, however it should be understood that if desired, the entire nail or rod system may be formed of one piece.

The distal portion 11 is preferably curved so as to follow the natural curvature of the femoral canal. It has been found that an appropriate radius for this curve would be about 127 cm in most cases, and the curve preferably commences about an inch below the junction of the proximal and distal portions of the nail. The curvature is best seen in FIG. 4.

At the open end of the distal portion 11, a guide nose or tip means 13 is provided which may be generally cylindrical with rounded edges as shown in FIG. 4, or rounded and of two piece construction as shown in FIG. 1. The nose serves to guide the nail during insertion.

It will be seen from FIG. 3 that in the preferred form, the distal portion 11 is hollow throughout. This hollow construction allows the use of guide wires during the insertion and provides pressure relief during insertion. The distal portion 11 is provided on its surface with a plurality of longitudinal flutes 15 throughout its length. The flutes terminate in pointed cutting ends 16. In order to effectively transmit both bending and torsional loads from the proximal fracture fragment to the distal fracture fragment, the nail or rod must fit closely in the medullary canal to allow the flutes to engage the cortical bone. It is for this reason that the distal portion of the nail is provided with flutes 15 and the pointed cutting tips or ends 16 which cut their own mating grooves in the medullary surface of the cortical bone during the force of insertion. A plurality of apertures 17 are drilled below the cutting tips 16. These holes preferably lead rearwardly at approximately a 45° angle and provide clearance room for bone chips and marrow to pass and to be collected within the cannula 14 of the nail.

Although the nail need not be cannulated through its entire length in the preferred design, cannulation carries throughout so that insertion may be facilitated through the use of a guide wire. In particular, the use of such a guide wire permits insertion of the nail by means of a "blind" technic without an operative incision being necessary at the fracture site. Thus, a sub-trochanteric fracture is not converted from a closed or sterile type of fracture to an open and possibly contaminated fracture. Hence the incidence of infection is much less than those procedures utilizing open technic which involve direct operative intervention at the fracture site as compared to the closed procedures.

The flutes 15 terminate in a rearwardly sloping portion as shown at 18 in FIG. 6 and a cylindrical extension 19 is directed rearwardly and longitudinally of the distal portion 11, and serves for interconnection with the hollow interior of the proximal portion 12.

Proximal portion 12 is formed with a bore 20 at its forward end terminating in a shoulder 21 which receives the cylindrical extension 19 of the distal portion 11. The proximal portion is hollow throughout and includes a cannula 22 and a somewhat larger diameter bore 23 at its rearward end. The proximal portion is typically straight and is also provided with a plurality of longitudinal flutes 24 which are designed to cut mating grooves in the cortical bone as well as in the less dense cancellous bone found in the flared or wider portion of the medullary canal of the proximal femur F. It will be noted from FIGS. 1 and 6 that the flutes 24 of the proximal portion are provided with a similar pointed cutting end and an undercut portion 25. This undercut portion provides sufficient room beneath and around the cutting edges to permit bone chips to accumulate therein without affecting the cutting function of the edges of the flutes. In effect, the undercut portion provides a function similar to that provided by the apertures 17 on the distal portion 11. If desired, however, similar apertures could be provided in the undercut portion.

It will be noted that in order to enhance the gripping characteristics of the nail in the proximal femur canal, the proximal portion 12 is formed with a larger diameter than that of the distal portion of the nail. The various diameter combinations of the nails are not limited as noted previously, however it has been found that the difference between the two diameters in each nail should be at least 1.5 mm. In use, actual ratios of 16:11, 16:13; 18:13 and 18:15 have been found to be practical.

A cap member 26 closes off the open end of the proximal portion 12 and is provided with an internal bore 27 which is tapped as shown at 28 for the reception of auxiliary instruments and tools. A flange or shoulder 29 is also provided on the cap and serves to prohibit distal migration of the nail during insertion. The flange is of course of a diameter greater than the greatest diameter of the proximal portion of the nail and its inner or distal surface is adapted to rest in the trochanteric notch of the femur thereby preventing the distal migration noted. In FIG. 1, T designates the trochanter of the femur and N shows the neck thereof. Both the cap member 26 and extension 19 of the distal portion may be secured within the proximal portion 12 of the nail in any known manner, however it has been found that electrobeam welding applied at W in FIG. 4 is an ideal means for rigidly and securely joining these elements.

A conventional extractor cap 30 shown in FIG. 7, having an eye 31 and a threaded stub shaft 32 may be inserted in the tapped bore of the cap 26 to aid in removal of the nail.

The sub-trochanteric rod set forth above may be formed of any known compatible metal that has been approved for implantation in the human body.

TECHNIC OF INSERTION

Preferably a small incision is made in the region of the greater trochanter T and then the cortex is pierced. A guide wire may be inserted through the incision and the proximal bone fragment across the fracture FR and into the distal fracture fragment. In the usual process of insertion, reaming of the proximal fracture segment to a larger diameter than the distal fracture segment using individual different diameter reamers or a one piece stepped diameter reamer is preferred. Although it is not absolutely necessary to ream the medullary canal to use the nail, it is the preferred method of insertion, for by reaming one fills the reamed medullary canal with the nominal or root diameter of the nail permitting larger flute diameters to engage the cortical bone. A cannulated or a stepped reamer is then passed over the guide wire and the medullary canals of both the fracture fragments are reamed. Following removal of the reamer, an appropriate sized sub-trochanteric rod or nail is selected and inserted over the guide wire and is driven in with conventional instrumentation to the appropriate depth as limited by flange 29. Preferably an impact hammer is used and may be directly attached to the proximal end of the nail or to another implantable or non-implantable appliance directly attached to the proximal portion of the nail. The impact instrument and guide wire are subsequently removed. If desired, an implantable extraction appliance of the type shown in FIG. 7 is attached in the bore 27 of the cap member 26. This device will permit subsequent removal of the nail with conventional extraction instrumentation.

While I have described the new sub-trochanteric rod in specific detail, it will be apparent that the rod may be modified or varied in many respects without departing from the invention. Other variations and alternatives may come within the scope of the following claims.

I claim:
1. A sub-trochanteric intramedullary rod for fracture fixation of long bones comprising an elongated generally cylindrical rod member having a major distal portion and a minor proximal portion, said proximal portion having a diameter greater than the distal portion, a plurality of longitudinal flutes spaced about the periphery of each of said portions, the flutes on said major portion terminating in sharp cutting points which extend beyond said portion.

2. A sub-trochanteric intramedullary rod as defined in claim 1 wherein the flutes on said minor portion terminate in sharp cutting points which extend beyond said portion.

3. A sub-trochanteric intramedullary rod as defined in claim 1 and further including guide tip means of lesser diameter than said major portion and extending from the distal end thereof.

4. A sub-trochanteric intramedullary rod as defined in claim 1 wherein said major portion is curved to follow the natural curvature of the long bone.

5. A sub-trochanteric intramedullary rod as defined in claim 4 wherein the radius of curvature is about 127 cm.

6. A sub-trochanteric intramedullary rod as defined in claim 1 wherein the difference between the diameters of said major and minor portions is at least 1.5 mm.

7. A sub-trochanteric intramedullary rod for fracture fixation of long bones comprising an elongated generally cylindrical rod member having a major distal portion and a minor proximal portion, said proximal portion having a diameter greater than said distal portion, a plurality of longitudinal flutes spaced about the periphery of each of said portions, said flutes terminating in sharp bone cutting projections which extend beyond the distal ends of said portions, and means adjacent said projections on said major portion for receiving and holding bone chips and the like.

8. A sub-trochanteric intramedullary rod as defined in claim 7 wherein said rod member is of hollow construction throughout and wherein said means for receiving and holding bone chips comprises a plurality of apertures in the surface of said rod member extending into communication with the hollow interior thereof.

9. A sub-trochanteric intramedullary rod as defined in claim 8 and further including an annular recess adjacent said projections on said minor portion for receiving and holding bone chips and the like.

10. A sub-trochanteric intramedullary rod as defined in claim 7, and further including guide tip means of lesser diameter than said major portion and extending from the distal end thereof.

11. A sub-trochanteric intramedullary rod as defined in claim 8 and further including an end cap secured to the proximal end of said minor portion and of larger diameter than said minor portion to serve as a limit stop during insertion.

12. A sub-trochanteric intramedullary rod as defined in claim 11 wherein said cap is provided with an internally threaded portion adapted for connection to rod extraction means.

* * * * *